United States Patent [19]

Prodi et al.

[11] 4,092,845
[45] June 6, 1978

[54] LUNG SIMULATING AEROSOL SAMPLER

[75] Inventors: Vittorio Prodi; Carlo Melandri; Giuseppe Tarroni, all of Bologna; Massimo Formignani, Ferrara; Tonino De Zaiacomo, Bologna; Gianfranco Bompane, San Lazzaro (Bo), all of Italy

[73] Assignee: Comitato Nazionale per l'Energia Nucleare — Cnen, Rome, Italy

[21] Appl. No.: 797,365

[22] Filed: May 16, 1977

[30] Foreign Application Priority Data

May 28, 1976 Italy .................... 49698 A/76

[51] Int. Cl.² .................... G01N 15/06
[52] U.S. Cl. .................... 73/28; 73/421.5 R
[58] Field of Search ............. 73/28, 421.5 R

[56] References Cited

U.S. PATENT DOCUMENTS 2,076,553 4/1937 Drinker et al. .................... 73/28

FOREIGN PATENT DOCUMENTS 592,818 9/1947 United Kingdom .......... 73/421.5 R

OTHER PUBLICATIONS

Marple; V. A., Impactors with Respirable Cut-off Characteristics; Particle Technology Labratory Publication No. 314, University of Minn., Minneapolis Minn., 55455.

Primary Examiner—S. Clement Swisher
Attorney, Agent, or Firm—Stevens, Davis, Miller & Mosher

[57] ABSTRACT

A simulator of the aerosol particle disposition in the human respiratory tract comprises a duct along which the following devices are included in the order: an air humidifier comprising a trunk with longitudinal partitions of blotted paper soaked with water, a cyclone, a vibrated bubbler comprising a cylindrical vertical vessel partially filled with water and provided with a pierced horizontal partition at a level lower than the water level within said vessel, a vacuum pump, a flowmeter. The air to be tested is passed through said duct for a predetermined time period and at a predetermined flow rate. Subsequent to said passage, physical, chemical, toxicological, radiometric analyses are carried out either on the water itself or on the solid therein contained or on both.

8 Cla

Fig. 2

LUNG SIMULATING AEROSOL SAMPLER

The object of this invention is an apparatus for determining the contamination of the air by aerosol particles liable to deposit in the human respiratory tract.

An apparatus of this class should be effective for providing fluid samples which, when analyzed, allow the assessment of the amount of aerosol particles present in the air to be breathed and liable to deposite on the human respiratory tract and particlularly on the lungs.

In other words, an apparatus of this class should be a simulator — as faithful as possible — of the human respiratory tract with respect to the capture of the aerosol particles A large number of experimental data are available on the deposition of aerosol particles in the human respiratory tract.

For the following discussion the data of curve D in FIG. 2 are assumed as representative of the deposition in the pulmonary region alone of an aerosol inhaled through the nose. Curve D shows the deposition percentage as a function of the aerosol particle size in the breathed air. For instance about 45% of the 2 $\mu$m particles and about 27% of the 1 $\mu$m particles inhaled are catched in the pulmonary region.

For a rational approach to the above problem, the human respiratory tract has been subdivided into regions of homogeneous behaviour from the fluidodynamic point of view and from the point of view of the absorption of the aerosol particles. A means should then be devised for separately simulating the behaviour of said regions from the same points of view. To this purpose it is customary to subdivide the respiratory tract into nasopharingeal (NF), tracheobronchial (TB) and pulmonary (P) regions. Such subdivision — which is generally accepted in the practical field of the industrial hygiene physics — is to be deemed valid both for the deposition mechanics of the particles, which are strongly dependent on the particle size, and for the removal mechanics of the particles.

The deposition is mainly inertial in the regions NF and TB and mainly by sedimentation and diffusion in region P.

As for the particles removal, this is by mechanical effects and by mucous transfer in regions NF and TB, while in region P it is by solubilization in vivo, by phagocytosis and by "transparency" through membranes. The removal in regions NF and TB is rapid, while in region P the aerosol particles stay longer, particularly in the case of insoluble substances. Thence the importance arises of assessing the aerosol fraction deposited in the P region.

According to the prior art, the first two regions (NF, TB) of the respiratory tract are simulated by a cyclone whose deposition efficiency, as a function of the particle size, follows a nominal curve which has been plotted by A C G I H (American Conference of Government Industrial Hygienists).

Such curve is shown in FIG. 4, the following being some of the deposition efficiencies therefrom:
10% of 2 $\mu$m particles
25% of 2.5 $\mu$m particles
50% of 3.5 $\mu$m particles
100% of 10 $\mu$m particles,
wherein by the term size the diameter is meant of a spherical particle of which the specific gravity is 1 g/cm$^3$.

According to the prior art, the following criterion is followed for simulating the third region (region P).

The air, outflowing from the above cyclone, is filtered by an absolute filter by which all the particles escaping from the cyclone are captured.

The empirical assumption is then made that the average amount of particles deposited in the human pulmonary region corresponds to 1/3 of the particles retained by the absolute filter.

It clearly appears that the above method is based on rather rough assumptions, the more because the pulmonary deposition depends mainly on diffusion.

The motivations of this invention are partially discussed in the article "Simulation of the regional deposition of aerosols in the respiratory tract" by C. Melandri and V. Prodi (American Industrial Hygiene Association Journal, Vol. 32, Jan. 1971).

The concepts therein exposed have been subsequently worked out with the aim of developing an operational apparatus readily constructible and accurately reproducible, effective for providing substantially constant results at comparable operative conditions.

The following considerations have been taken as a guidance in developing the apparatus of this invention.

a. The deposition in the naso-pharigeal and tracheobronchial regions is due mainly (but not exclusively) to inertial and gravitational effects.

A selective cyclone was deemed therefore to be the best suited means for simulating the deposition in said regions of which the path is actually rather tortuous.

Such approach is the same as practised by the prior art.

However, differently from the prior art, a humidifying stage was added upstream of the cyclone, which stage comprises a duct provided with longitudinal partitions made of blotting paper which is kept constantly moist. In such a way the incoming air is humidified and the size of the aerosol particles both hygroscopic and soluble grows the same way as along the respiratory tract.

By adding such humidifying stage, a closer approach than in the past was attained to the experimental data by Dautrebande and Walkenhorst (see the article by the same authors "Über die Retention von Kochsaltztellchen in den Atemwegen" published in "Haled Particles and Vapours" edited by C. N. Davis, pp 110–120 — Pergamon Press, Oxford 1951).

b. A bubbler has been adopted for simulating the deposition in the region P.

In fact it has been found that the aerosol particles in an air bubble which rises through a liquid are deposited onto the same liquid with a mechanism which closely approaches the deposition of similar particles in the respiratory tract. This applies also to the submicromic particles which are deposited preferably in the pulmunary region.

The main object of this invention is therefore the provision of an apparatus for simulating as closely as possible the behaviour of the human respiratory tract from the point of view of the deposition of the inhaled aerosol particles.

Another object of this invention is to provide an apparatus as above outlined effective for quantitatively assessing the aerosol particles deposited in the pulmonary region.

A further object of this invention is to provide an apparatus adapted for simulating the respiratory tract as a whole, that is effective for capturing the aerosol particles contained in the processed air — the same fraction thereof as in the respiratory tract — in a single passage through the apparatus without any need for successively processing the same batch of air by means of separate sampler.

Still another purpose of this invention is to provide an apparatus having a low cost simple structure, readily and exactly reproducible in quantity production, whereby complicated and time consuming calibrations of each produced unit are avoided.

A further object of this invention is an apparatus effective for reproducing the operational characteristics of the respiratory tract but at a flow rate considerably greater than that of a single person, whereby the required amounts of samples to be analyzed are collected in a limited period of time and thus the sampling operations are greatly speeded up.

Basing on the above concepts an apparatus has been constructed wherein the following assemblies are serially connected: a humidifying stage wherein the air to be processed is humified and the coarser particles are caught by gravitational sedimentation; a cyclone for capturing the particles by inertia; a bubbler for capturing the particles by sedimentation, inertia and diffusion; a vacuum pump and a flow meter.

This invention will be better understood from the following description and attached drawings which illustrate by way of example a preferred embodiment thereof.

In the drawings:

FIG. 1 shows a diagram of the apparatus of this invention;

FIG. 2 shows the deposition graph (A) of the first stage of the apparatus, the deposition graph (B) of the combined first and second stages of the apparatus; the deposition graph (C) of the third stage singularly considered but connected downstream of the first two stages of the apparatus and the graph (D) of the deposition in the pulmonary region of the human respiratory tract from air which has passed through the nasopharyngeal and tracheobronchial regions, that is the deposition occurring in the case of air inhaled and exhaled through the nose.

In all the above graphs, the deposition efficiency — that is the percentage amount deposited of the total contained in the processed air — is plotted against the geometrical particle sizes.

Figure 1:
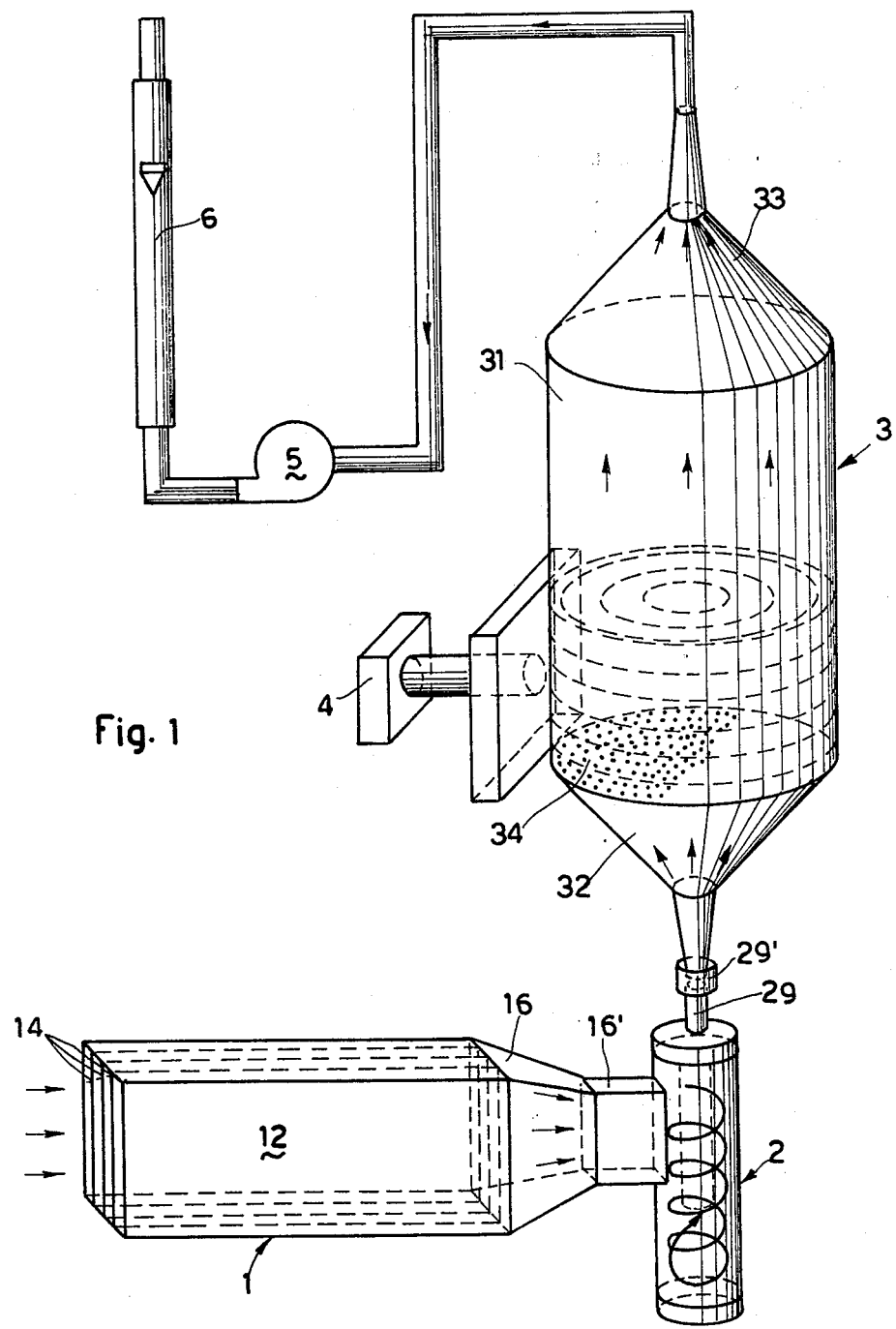

With reference to the drawings and particularly to FIG. 1, the apparatus of this invention comprises a humidifying and capturing means consisting of a duct 12 with rectangular cross section which is provided with a plurality of vertical partitions 14 made of blotting paper regularly spaced and extending from the duct bottom to the ceiling thereof. One end of the duct is open and functions as the air intake. The floor is constantly flooded with water so that the partition paper is constantly soaked with water. The other end of duct 12 communicates with the inlet slot of a cyclone of novel structure through a tapered connection 16 and a nozzle 16'. Cyclone 2 comprises a hallow cylinder 22 with inwardly threaded ends. At one end a solid plug is threadingly engaged to form a seal with an "O" ring — if so required — inserted between the plug and the cylinder. At the other end of tube 22 a plug is screwed provided with a central through bore 28'. The distance between the inner surfaces of plugs 24, 28 is about 3.5 times the inner diameter of tube 22. A coaxial cylindrical extension projects from each end surface of plug 28, which extension has an inner bore of the same diameter as the plug and an outer diameter much smaller than the plug. One 27 of said extensions projects from the plug inwardly of cylinder 22 for a distance about 4/5 the distance between the inner surfaces of plugs 24 and 28. The outer diameter of extension 27 is about one half of the inner diameter of tube 22, so that a whirling space is defined between extension 27 and the inner wall of tube 22. Extension 29 functions as a connection of the cyclone with the rest of the apparatus.

Figure 3A:
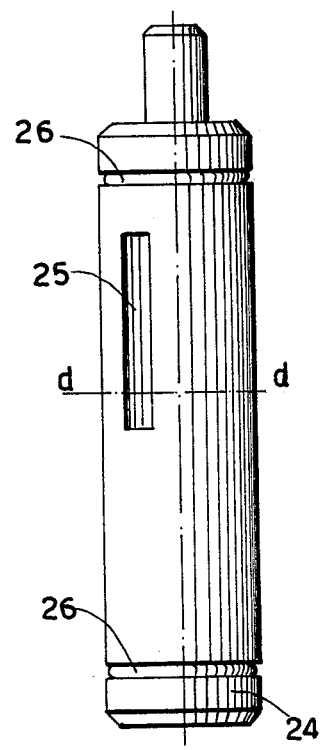
FIGS. 3a, 3b, 3c and 3d show respectively a side view, a laongitudinal cross section, a top plan view and a cross section of the cyclone included in the apparatus of this invention.
Figure 3B:
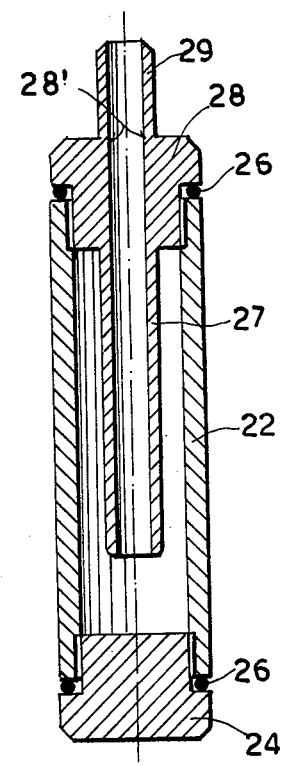
Figure 3C:
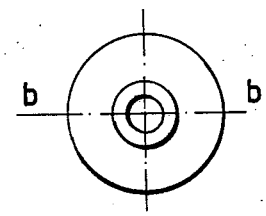
Figure 3D:
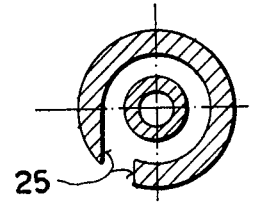
Figure 4:
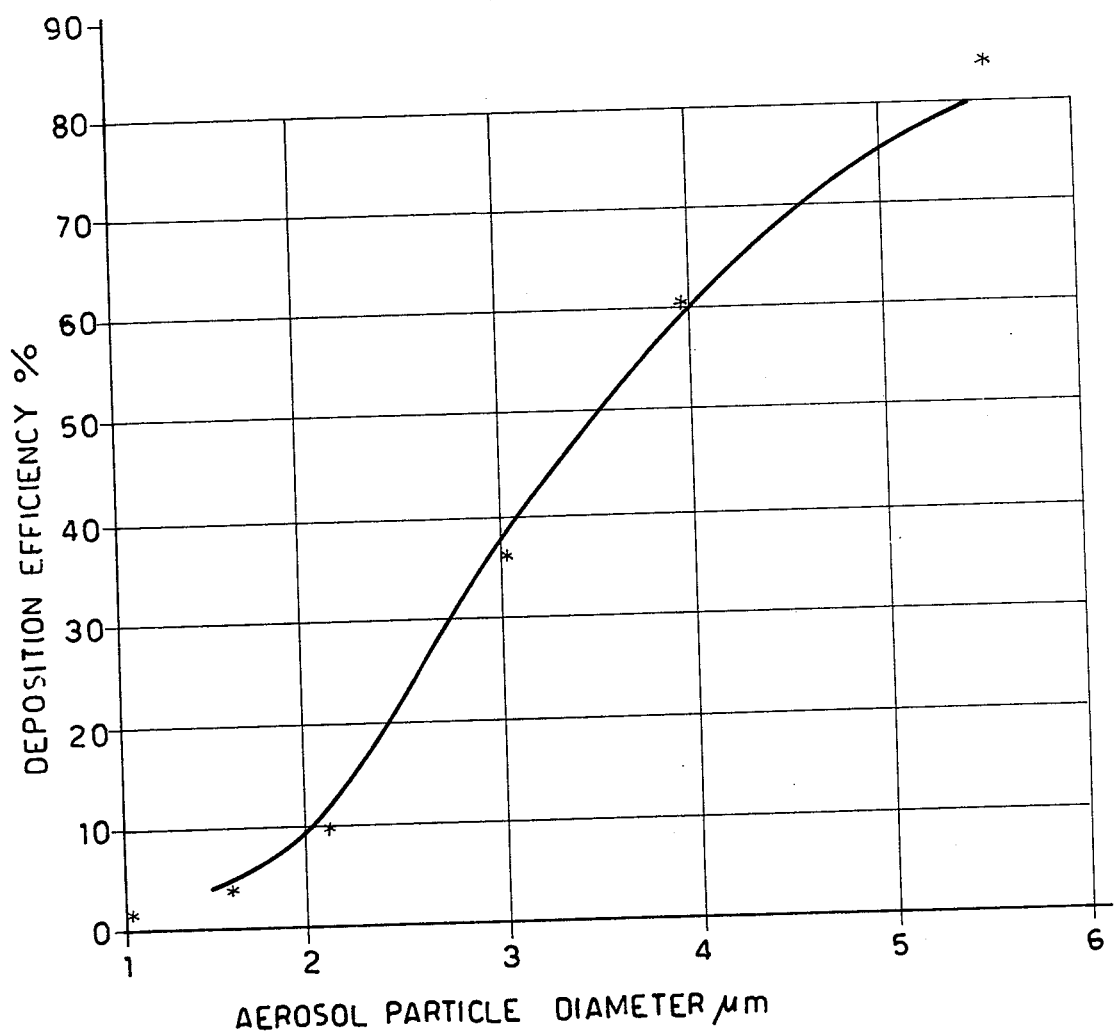
FIG. 4 shows a deposition graph in the cyclone of FIGS. 3a, 3b, 3c, and 3d.

Tube 22 is provided with an inlet slot 25 of the air into the cyclone and, as shown in FIG. 3d, it has a rectangular cross section.

One of the two longer sides of the slot lies on a plane parallel to the axis of tube 22 and tangent to the inner surface of the same tube; the other longer side lies on a plane parallel to said plane of the first side and inwardly offset from it. Slot 25, when projected on a plane perpendicular to the above parallel planes, has its shorter dimension about equal to the difference between the outer radius of extension 27 and the inner radius of tube 22; its longtitudinal dimension extends from the inner surface of plug 28 to about one half of the distance between the two plugs.

The above described cyclone has an extremely simple structure so that it can be exactly replicated with the assuredness that the deposition caracteristics of the prototype will be maintained constant in quantity produced units. This cyclone, when operated at a flow rate of 25 l/sec can be employed as the first stage of a selective sampler in combination with an absolute filter as known in the prior art. The cyclone outlet comprising extension 29 communicates through elastic coupling 29' with a bubbling column 3.

Column 3 comprises a vertical cylindrical vessel which terminates with two cones, an upper one 33 and a lower one 32. The cylindrical section 31 and the lower cone 32 are separated by a sieve plate 34 which is an important feature of this invention. The diameters of its holes and their distribution are critical factors of the apparatus effectiveness.

In operation column 3 is partially filled with liquid.

To column 3 a vibrator 4 is associated adapted for imparting transverse vibration to the column; its purpose is for causing the bubbles which form on the upper surface of sieve plate 34 to become detached therefrom when they are grown to a certain size and for preventing the rising bubbles to move along preferential paths and coalesce into bubbles of greater size whereby the deposition efficiency would change from one bubble to another.

Upper cone 33 communicates with a vacuum pump through an elastic coupling not shown and a pipe 5', a flowmeter being connected downstream of vacuum pump 5.

OPERATION

Column 3 is first shut off from cyclone 2 by means of a gate valve not shown.

Vacuum pump 5 and vibrator 4 are started. Cyclone 2 and column 3 are connected together. Column 3 is then partially filled with an amount of liquids such that the required liquid head on plate 34 is attained in steady operation. After attaining a steady flow rate by adjustment of suitable valves, not shown, and by checking said flow rate by means of flow meter 6, the time count is started.

At the end of the scheduled run, the connection between cyclone 2 and column 3 is shut off, vacuum pump 5 and vibrator 4 are stopped and the liquid is drained from column 3.

On the drained liquid all the analyses can be carried out for the toxicological evaluations. For instance, the soluble and insoluble contaminations can be separately determined by filtering the liquid through a membrane filter; radiometric determinations and micromechanical analyses can be carried out both on the liquid itself and on the solid content or on the filtrate.

EXAMPLE

An apparatus according to this invention has been constructed to meet the following specification.
Flow rate: 45 l/1 feet
First stage (humidifying and capturing stage) comprising a a duct with square 7 × 7 cm, 25 cm long, in which 10 longitudinal partitions of blotting paper are enclosed.
Second stage comprising a cyclone with the following dimensions:
    inlet slot 25: 3.25 × 0.5 cm cross section,
    inner diameter of deposition tube 22: 1.8 cm,
    distance between plugs: 6.5,
    outer diameter of inner extension 27: 1.00 cm
    inner diameter of inner and outer estensions 27, 29: 0.6 cm,
    inner extension length: 5.2 cm.
Third stage (bubbler) main data:
    inner diameter of cylinder 31: 15.0 cm,
    thickness of sieve plate 34: 0.06 cm,
    number of through holes of sieve plate: 500,
    pattern of hole of the sieve plate: square grid of 0.6 cm pitch. That is the holes are at the intercrossing of two arrays perpendicular therebetween, of parallel lines uniformly spaced at 0.6 cm intervals,
    diameter of holes: 0.08 cm,
    liquid (water) head: 10.0 cm,
    vibrator 4 frequency: 10 Hz,
    vibration amplitude: 0.1 cm.

Figure 2:
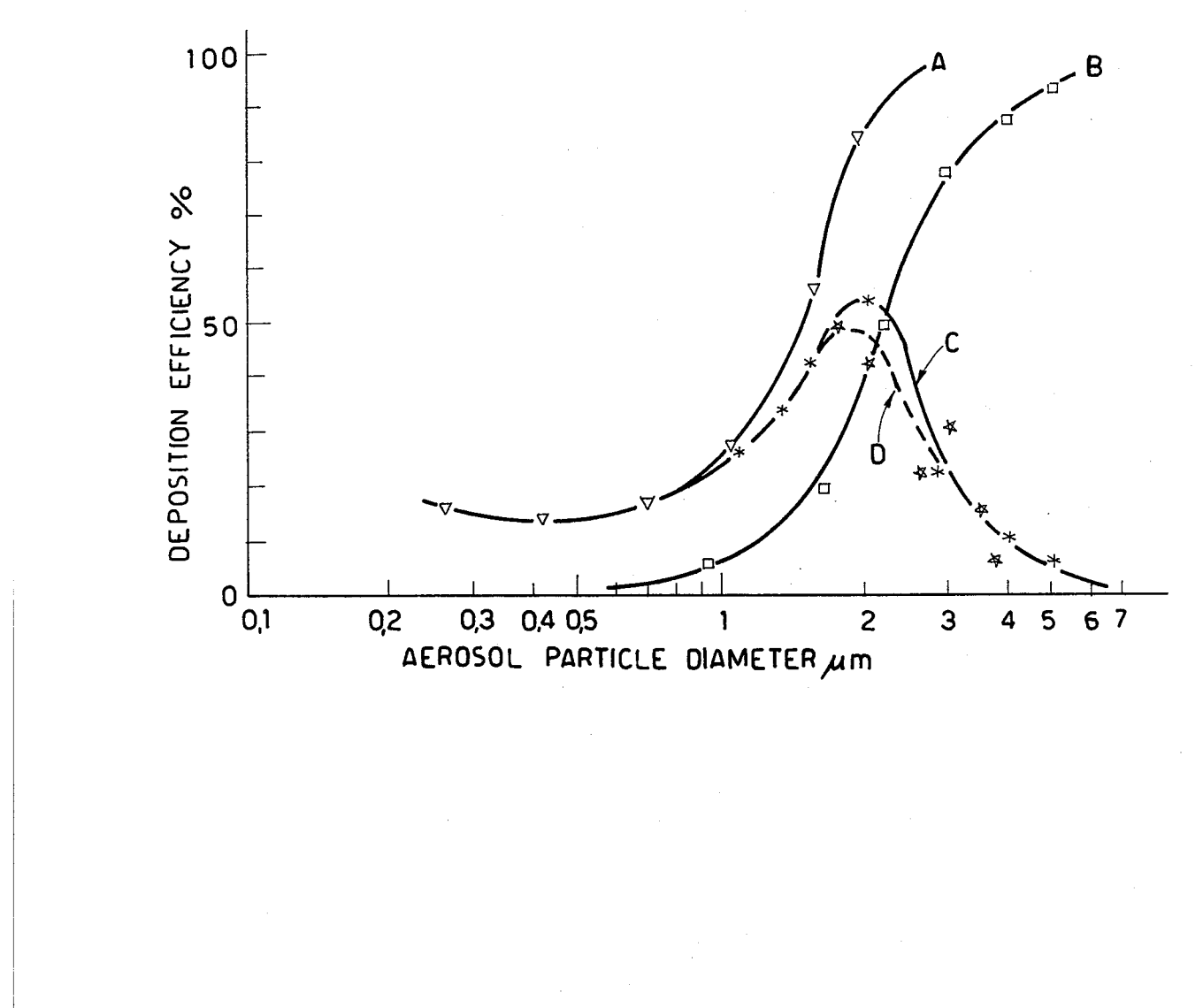

The granulometry of the particles contained in the water drained from bubbler 3 has been determined and the related data have been plotted against the deposition efficiency as shown by curve C of FIG. 2.

As it appears from FIG. 2, curve C is in fair agreement with curve D which is the experimental deposition curve in the pulmonary region. Curve C can therefore be taken as representative of the aerosal particle deposition in the region of toxicological interest.

In cost and operational time the apparatus and method of this invention are comparable, if not better than the prior art methods and apparatuses but they greatly surpass them in accuracy and in approximation to the actual pattern of the phenomenon, particularly with respect to the deposition by browian effect and to the hygroscopy particle growth along the respiratory tract.

A preferred embodiment of the invention has been thus described. Many modifications and variants can be envisaged by those skilled in the art; however such modifications and variants are intended to fall within the scope of the appended claims whenever they are made in the true spirit of this invention.

We claim:

1. An apparatus for simulating the human respiratory tract with respect to the deposition of aerosol particles contained in the breathed air which apparatus comprises an enclosed duct along which the following means are included in the order: a humidifying and particle catching means; a cyclone; a bubbler and a vacuum pump.

2. An apparatus as claimed in claim 1, wherein said humidifying means comprises a duct with generally rectangular cross section provided with blotting paper longitudinal partitions or fins therewithin which vertically extend from the duct floor this being constantly flooded with water.

3. An apparatus as claimed in claim 1, wherein said cyclone comprises a cylindrical metal tube with a plug at each end, one plug being blind and the other being provided with a central bore which extends through a first cylindrical projection at the outer face of the plug and through a second cylindrical projection at the inner face thereof; said first projection extending from the plug for a short distance to form a connection fitting and said second projection extending to nearly reach the inner surface of said blind plug; said cylinder being provided with a rectangular slot of which the longer sides lie on planes parallel to the tube axis the plane of one side being tangent to the inner surface of the tube and the plane of the other side being inwardly offset and about tangent to the outer diameter of said second projection; the dimensions of the shorter sides of the slot cross section being about equal to the difference between the inner radius of said tube and the outer radius of said second projection, while the longer sides extend from the inner face of the bored plug to about one half of the distance between the two plugs.

4. An apparatus as claimed in claim 1 wherein said bubbler comprises a vertical cylindrical vessel which terminates with an upper and a lower cone, a sieve plate being inserted between the cylindrical section of said vessel and the lower cone to separate them from one another, the lower cone being connected to the outlet of said cyclone while the upper cone is connected to said vacuum pump; said cylindrical section being partially filled with a liquid.

5. An apparatus as claimed in claim 4, which apparatus is provided with a vibrator associated with said bubbler for vibrating it transversely.

6. An apparatus as claimed in claim 4 wherein said sieve plate is a metal plate 0.6 mm thick provided with through holes of 0.8 mm diameter which holes are at the crossing at a square grid of 6 mm pitch and the liquid head on the plate is 100 mm.

7. An apparatus as claimed in claim 6 wherein said liquid is water.

8. A method for the determination of the aerosol particles in the air to be breathed and liable to deposit in the pulmonary region of the human respiratory tract, which method comprises the steps of passing the air to be sampled through the apparatus of claim 1 for a predetermined time interval at a predetermined flow rate, assessing the particles deposited in the liquid of said bubbler and their nature.

* * * * *